(12) United States Patent
Morikawa et al.

(10) Patent No.: US 9,958,949 B2
(45) Date of Patent: May 1, 2018

(54) BIOLOGICAL POTENTIAL INPUT INTERFACE SYSTEM, SENSOR DEVICE, AND METHOD

(71) Applicant: Panasonic Intellectual Property Management Co., Ltd., Osaka (JP)

(72) Inventors: Koji Morikawa, Kyoto (JP); Tsuyoshi Inoue, Nara (JP); Koichi Ikemoto, Hyogo (JP); Satoshi Kanai, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 518 days.

(21) Appl. No.: 14/665,630

(22) Filed: Mar. 23, 2015

(65) Prior Publication Data
US 2015/0261307 A1 Sep. 17, 2015

Related U.S. Application Data

(63) Continuation of application No. PCT/JP2014/003366, filed on Jun. 23, 2014.

(30) Foreign Application Priority Data

Jun. 24, 2013 (JP) .................................. 2013-131366

(51) Int. Cl.
*G09G 5/00* (2006.01)
*G06F 3/01* (2006.01)
(Continued)

(52) U.S. Cl.
CPC ............ *G06F 3/017* (2013.01); *A61B 5/0488* (2013.01); *A61B 5/681* (2013.01); *G06F 1/163* (2013.01);
(Continued)

(58) Field of Classification Search
CPC .................................. G06F 1/163; A44C 5/22
(Continued)

(56) References Cited

U.S. PATENT DOCUMENTS 6,380,923 B1 * 4/2002 Fukumoto ............... G06F 1/163
341/22
8,170,656 B2 5/2012 Tan et al.
(Continued)

FOREIGN PATENT DOCUMENTS

| JP | H03-85614 U | 8/1991 |
| JP | H05-037482 U | 5/1993 |
| JP | 2007-089676 A | 4/2007 |

OTHER PUBLICATIONS

Form PCT/ISA/210 for corresponding International Application No. PCT/JP2014/003366, dated Aug. 5, 2014.

*Primary Examiner* — Abdul-Samad A Adediran
(74) *Attorney, Agent, or Firm* — Renner, Otto, Boisselle & Sklar, LLP

(57) ABSTRACT

A sensor device includes a plurality of electrode chambers, a measurement chamber, and an accommodation chamber which are connected in annular relationship permitting expansion and contraction. Each of the plurality of electrode chambers has a measurement electrode. The measurement chamber has a biological potential measurement circuit which is connected with each measurement electrode via electrically conductive wiring for measuring biological potential of the user by using the measurement electrode. The accommodation chamber has an internal protrusion. The wiring which connects at least one measurement electrode and the biological potential measurement circuit is provided around the protrusion, the wiring having a length which enables longitudinal feeding in accordance with an amount of elongation when the sensor device is elongated. A maximum clearance S between the accommodation cham-
(Continued)

ber and an adjacent chamber is greater than a maximum clearance R between any two adjacent chambers.

10 Claims, 15 Drawing Sheets

(51) Int. Cl.
*G06F 1/16* (2006.01)
*A61B 5/0488* (2006.01)
*A61B 5/00* (2006.01)
*A61B 5/0492* (2006.01)

(52) U.S. Cl.
CPC .............. *G06F 3/014* (2013.01); *G06F 3/015* (2013.01); *A61B 5/0492* (2013.01)

(58) Field of Classification Search
USPC ............................................ 341/22; 368/282
See application file for complete search history.

(56) References Cited

U.S. PATENT DOCUMENTS

| 8,447,704 | B2 | 5/2013 | Tan et al. |
| 2005/0237864 | A1* | 10/2005 | Albisetti ................. A44C 5/22 368/282 |
| 2009/0327171 | A1 | 12/2009 | Tan et al. |
| 2013/0150697 | A1 | 6/2013 | Imai et al. |

* cited by examiner

|  |  | young adults | | | elderlies | | |
|---|---|---|---|---|---|---|---|
|  |  | M | F | M+F | M | F | M+F |
| Percentile | 2.5 | 231.3 | 210.1 | 212.0 | 224.4 | 200.9 | 205.4 |
|  | 5 | 234.7 | 212.0 | 214.0 | 227.2 | 205.4 | 211.7 |
|  | 10 | 240.3 | 214.0 | 219.0 | 232.6 | 211.7 | 217.0 |
|  | 25 | 248.3 | 220.0 | 226.0 | 239.0 | 221.0 | 226.0 |
|  | 50 | 258.5 | 226.0 | 242.0 | 249.0 | 226.5 | 238.0 |
|  | 75 | 269.0 | 235.0 | 259.0 | 262.0 | 237.8 | 253.0 |
|  | 90 | 280.0 | 245.0 | 273.0 | 269.6 | 250.3 | 265.4 |
|  | 95 | 287.0 | 250.7 | 281.0 | 275.0 | 261.2 | 272.1 |
|  | 97.5 | 290.0 | 252.0 | 287.0 | 277.0 | 270.8 | 277.0 |
|  | N | 214 | 203 | 417 | 49 | 50 | 99 |
|  | Mean | 259.2 | 228.1 | 244.0 ** | 249.9 | 230.0 | 239.8 ** |
|  | S.D. | 15.66 | 12.26 | 21.01 ** | 15.16 | 17.51 | 19.13 ns |
|  | Min. | 221.0 | 197.0 | 197.0 | 221.0 | 198.0 | 198.0 |
|  | Max. | 302.0 | 281.0 | 302.0 | 284.0 | 287.0 | 287.0 |
|  | Skewness | 0.177 ns | 0.933 ** | 0.345 ** | 0.222 ns | 0.948 ** | 0.247 ns |
|  | Kurtosis | −0.182 ns | 1.887 ** | −0.677 ** | −0.671 ns | 1.681 * | −0.346 ns |
| LITERA-TURE | JASDF1 | 265.4 ** | 237.1 ** | -- | -- | -- | -- |
|  | JASDF2 | 265.1 ** | -- | -- | -- | -- | -- |
|  | IPRI67 | -- | -- | -- | -- | -- | -- |
|  | Hoshi | 248.6 ** | 218.1 ** | -- | -- | -- | -- |
|  | JLIA | -- | -- | -- | -- | -- | -- |
|  | JIS | -- | -- | -- | -- | -- | -- |
|  | USAF NOTE | -- | 234.8 | -- | -- | -- | -- |

NOTE: MEASURED AT A POSITION WHICH IS 6 mm DISTAL FROM BENT POSITION WHEN ELBOW IS BENT AT RIGHT ANGLE.

| MOTION | MANIPULATION OF DEVICE TO BE CONTROLLED 102 |
|---|---|
| a  | POWER OFF |
| b  | ... |
| c  | ... |

⋮

BIOLOGICAL POTENTIAL INPUT INTERFACE SYSTEM, SENSOR DEVICE, AND METHOD

This is a continuation of International Application No. PCT/JP2014/003366, with an international filing date of Jun. 23, 2014, which claims priority of Japanese Patent Application No. 2013-131366, filed on Jun. 24, 2013, the contents of which are hereby incorporated by reference.

BACKGROUND

1. Technical Field

The present disclosure relates to a biological potential input interface technique where an appliance is manipulated by using biological potential (e.g., myoelectric potential).

2. Description of the Related Art

U.S. Pat. No. 8,170,656 (hereinafter "Patent Document 1") and U.S. Pat. No. 8,447,704 (hereinafter "Patent Document 2") disclose interfaces which utilize electromyograms.

The interfaces described in Patent Documents 1 and require accurate measurement of the user's biological potential.

SUMMARY

Since every user has different physical features, the biological potential needs to be measured in a manner adapted to the user's physical features.

In order to solve the above problem, one implementation of the present invention encompasses a biological potential input interface system. The biological potential input interface system includes: a sensor device configured to measure biological potential of a user; a determination circuit configured to determine a motion of the user from the biological potential of the user against a determination criterion which is prepared in advance, and generate a control signal corresponding to the motion; and a control circuit configured to control operation of an internal circuit of an appliance based on the control signal. The sensor device includes a plurality of electrode chambers, a measurement chamber, and an accommodation chamber which are connected in annular relationship permitting expansion and contraction. Each of the plurality of electrode chambers has a measurement electrode. The measurement chamber has a biological potential measurement circuit which is connected with each measurement electrode via electrically conductive wiring for measuring biological potential of the user by using the measurement electrode. The accommodation chamber has an internal protrusion. The wiring which connects at least one measurement electrode and the biological potential measurement circuit is provided around the protrusion, the wiring having a length which enables longitudinal feeding in accordance with an amount of elongation when the sensor device is elongated. A maximum clearance S between the accommodation chamber and an adjacent one of the electrode chambers is greater than a maximum clearance R between any two adjacent electrode chambers among the plurality of electrode chambers.

The aforementioned general or specific implementation can be realized by using a system, a method, or a computer program, or alternatively by a combination of a system, a method, and a computer program.

A biological potential input interface according to the present disclosure adapts itself to the thickness of a site at which a user wears a sensor.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

DETAILED DESCRIPTION

Figure 1:
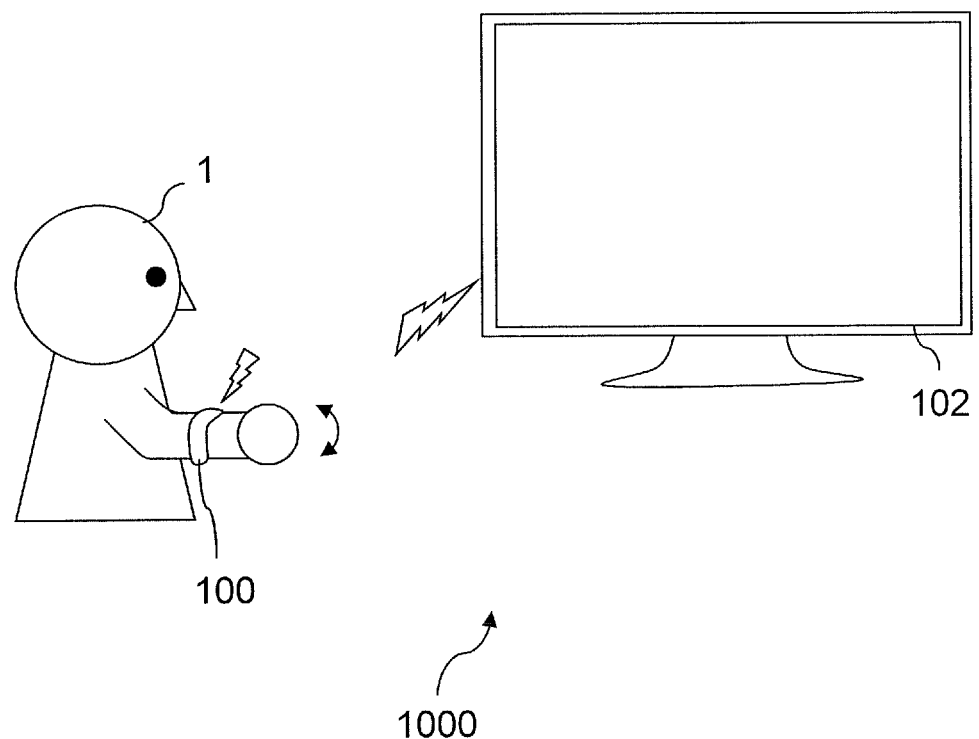
FIG. 1 is a diagram showing an implementation of a biological potential input interface system 1000 according to an exemplary embodiment.

In view of different physical features of different users, the inventors have explored constructions suitable for measuring biological potential in an adaptable manner to such different physical features. Thus, the inventors have arrived at a sensor device that can expand or contract according to the thickness of a site (e.g., a forearm) at which a user wears the sensor, as well as a biological potential input interface system including such a sensor device.

One implementation of the present invention is as follows, in outline.

A biological potential input interface system as one implementation of the present invention includes: a sensor device configured to measure biological potential of a user; a determination circuit configured to determine a motion of the user from the biological potential of the user against a determination criterion which is prepared in advance, and generate a control signal corresponding to the motion; and a control circuit configured to control operation of an internal circuit of an appliance based on the control signal. The sensor device includes a plurality of electrode chambers, a measurement chamber, and an accommodation chamber which are connected in annular relationship permitting expansion and contraction. Each of the plurality of electrode chambers has a measurement electrode. The measurement chamber has a biological potential measurement circuit which is connected with each measurement electrode via electrically conductive wiring for measuring biological potential of the user by using the measurement electrode. The accommodation chamber has an internal protrusion. The wiring which connects at least one measurement electrode and the biological potential measurement circuit is provided around the protrusion, the wiring having a length which enables longitudinal feeding in accordance with an amount of elongation when the sensor device is elongated. A maximum clearance S between the accommodation chamber and an adjacent one of the electrode chambers is greater than a maximum clearance R between any two adjacent electrode chambers among the plurality of electrode chambers.

A sensor device as another implementation of the present invention is for use in a biological potential input interface system including: a determination circuit configured to determine a motion of the user from the biological potential of the user against a determination criterion which is prepared in advance, and generate a control signal corresponding to the motion; and a control circuit configured to control operation of an internal circuit of an appliance based on the control signal. The sensor device for measuring biological potential of a user includes a plurality of electrode chambers, a measurement chamber, and an accommodation chamber which are connected in annular relationship permitting expansion and contraction. Each of the plurality of electrode chambers has a measurement electrode. The measurement chamber has a biological potential measurement circuit which is connected with each measurement electrode via electrically conductive wiring for measuring biological potential of the user by using the measurement electrode. The accommodation chamber has an internal protrusion. The wiring which connects at least one measurement electrode and the biological potential measurement circuit is provided around the protrusion, the wiring having a length which enables longitudinal feeding in accordance with an amount of elongation when the sensor device is elongated. A maximum clearance S between the accommodation chamber and an adjacent one of the electrode chambers is greater than a maximum clearance R between any two adjacent electrode chambers among the plurality of electrode chambers.

In one embodiment, a sensor device further includes a determination circuit configured to determine, from a biological potential of the user, a motion of the user that corresponds to the biological potential of the user. The biological potential measurement circuit is able to detect the biological potential of the user which occurs in accordance with the motion of the user.

In one embodiment, the determination circuit includes: a detection circuit configured to detect, when the biological potential measured by using the measurement electrodes satisfies a prestored detection criterion, that the user has made an intentional motion; and a motion determination circuit configured to, when the intentional motion is detected, determine the intentional motion of the user from the biological potential measured by using each measurement electrode against a determination criterion which is prepared in advance, and generate a control signal corresponding to the motion.

In one embodiment, the determination circuit includes: a detection circuit configured to detect, when the biological potential measured by using the measurement electrodes satisfies a prestored detection criterion, a point in time at which the biological potential is measured; and a motion determination circuit configured to detect an intentional motion of the user against a determination criterion which is prepared in advance, from the biological potential in a time range after a predetermined time since the detected point in time.

In one embodiment, each measurement electrode is provided in a respective one of the plurality of electrode chambers so as to be located on an inner peripheral surface of the sensor device being connected in annular relationship.

In one embodiment, in the sensor device being connected in annular relationship, the measurement chamber and the accommodation chamber are placed in substantially opposite positions from each other.

In one embodiment, in the sensor device being connected in annular relationship, the accommodation chamber is located in an asymmetric position from the measurement chamber with respect to a center of a circle.

In one embodiment, the determination circuit refers to a prestored manipulation reference in generating a control signal corresponding to a motion of the user from the biological potential measured by using each measurement electrode.

A method as still another implementation of the present invention is a method to be performed in a biological potential input interface system, including the steps of: providing a sensor device with which to measure biological potential of a user; and determining a motion of the user from the biological potential of the user against a determination criterion which is prepared in advance, and generating a control signal corresponding to the motion; and controlling operation of an internal circuit of an appliance based on the control signal. The sensor device includes a plurality of electrode chambers, a measurement chamber, and an accommodation chamber which are connected in annular relationship permitting expansion and contraction. Each of the plurality of electrode chambers has a measurement electrode. The measurement chamber has a biological potential measurement circuit which is connected with each measurement electrode via electrically conductive wiring for measuring biological potential of the user by using the measurement electrode. The accommodation chamber has an internal protrusion. The wiring which connects at least one measurement electrode and the biological potential measurement circuit is provided around the protrusion, the wiring having a length which enables longitudinal feeding in accordance with an amount of elongation when the sensor device is elongated. A maximum clearance S between the accommodation chamber and an adjacent one of the electrode chambers is greater than a maximum clearance R between any two adjacent electrode chambers among the plurality of electrode chambers.

A biological potential input interface according to an illustrative embodiment of the present invention includes a biological potential measurement circuit which, with a plurality of electrodes worn on the circumference of a forearm of a user, measures a potential difference between electrodes that occurs in connection with a hand motion. From changes over time of the potential difference measured by the biological potential measurement circuit, this interface utilizes a motion of a hand of the user as a control signal for an appliance. The distance between the plurality of electrodes is adjustable in order to adapt to varying forearm girth of the user, such that the adjustable range between electrodes is non-uniform.

Hereinafter, with reference to the attached drawings, an embodiment of the biological potential input interface system will be described.

Embodiment 1

FIG. 1 shows an exemplary implementation of a biological potential input interface system 1000. The biological potential input interface system 1000 includes a biological potential sensor device 100 and an appliance 102. The appliance 102 is the target of control in the biological potential input interface system 1000. Although FIG. 1 shows a user 1 who uses the biological potential input interface system 1000, the user 1 is not part of the construction of the biological potential input interface system 1000. Hereinafter, the biological potential input interface system 1000 may simply be referred to as the "interface system 1000", and the biological potential sensor device simply as the "sensor device".

The sensor device 100 is worn by the user 1.

Figure 2A:
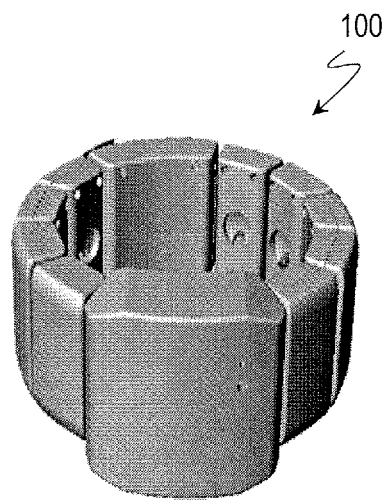
FIGS. 2A, 2B, and 2C are diagrams showing the appearance of a biological potential input interface system 1000 according to an exemplary embodiment.
Figure 2B:
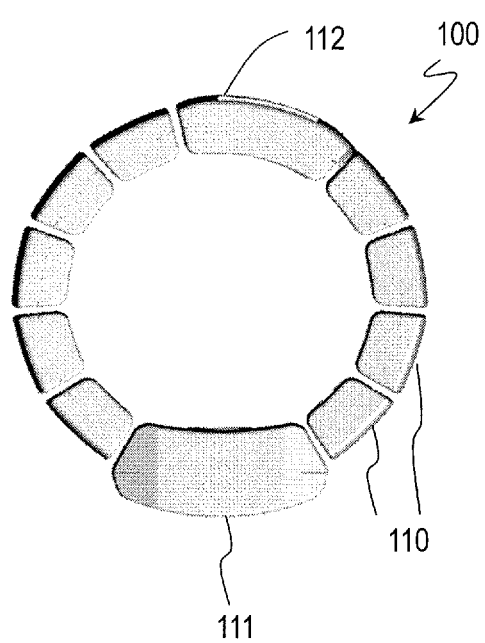
Figure 2C:
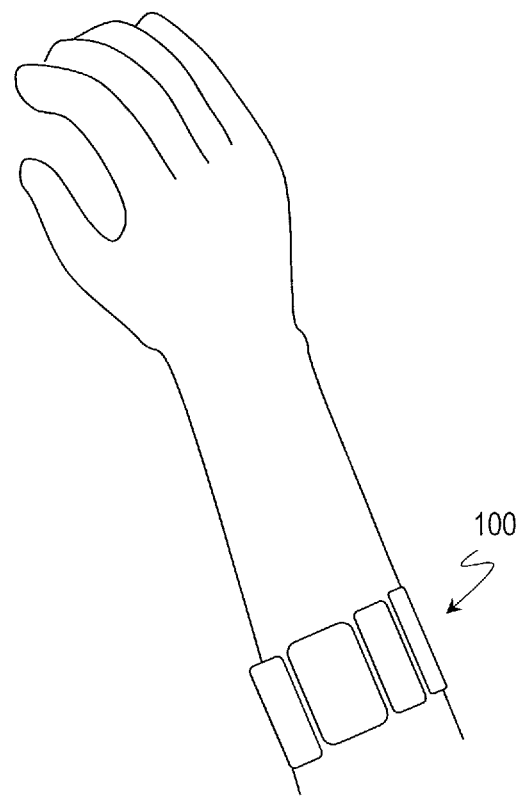

FIGS. 2A and 2B show an exemplary shape of the sensor device 100. The sensor device 100 is formed in annular shape, so as to be capable of expanding and contracting. As shown in FIG. 2B, the sensor device 100 includes a plurality of electrode chambers 110, a measurement chamber 111, and an accommodation chamber 112, which are connected in annular relationship. FIG. 2C shows an example where the sensor device 100 is worn on an arm of the user 1. The details of the sensor device 100 will be described later.

The user 1 makes a predetermined gesture while wearing the sensor device 100. This gesture is associated with a manipulation of the appliance 102. The sensor device 100 measures the biological potential while the user 1 is making the gesture. Biological potential means a potential which occurs in response to a gesture of a user. An example of biological potential of the user 1 is myoelectric potential.

The sensor device 100 refers to prestored references, and recognizes a gesture of the user 1 that corresponds to the measured biological potential. The sensor device 100 sends to the appliance 102 a manipulation instruction (control signal) corresponding to the recognized gesture. In the present embodiment, the control signal is sent wirelessly by using existing communications methods such as Wi-Fi®, Bluetooth®, ZigBee®, and Specified Low Power Radio.

Receiving the control signal, the appliance 102 controls the operation of its own internal circuit. Thus, by making a gesture, the user is able to operate the appliance 102 so as to perform a manipulation that is associated with that gesture. Examples of the appliance 102 are display devices including TV sets, appliances of video information recording/reproduction including BD recorders, and electronic devices including illumination devices and the like.

Now, prior to describing the constituent elements of the interface system 1000 in detail, findings of the inventors will be described first.

The inventors have realized that different physiques of users need to be taken into consideration in order to accurately measure the biological potential of a user. For example, the aforementioned Patent Documents 1 and lack detailed disclosure as to differing thicknesses of sites where users may wear a sensor (e.g., an arm), or how to cope with such differences.

Figure 3A:
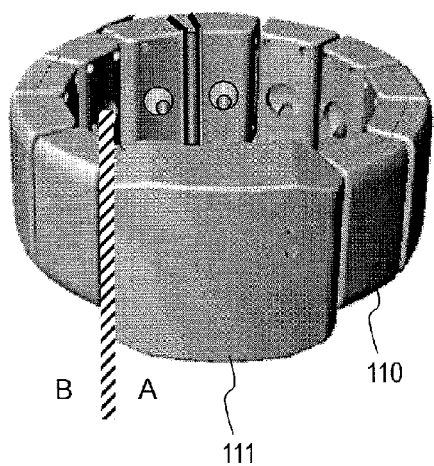
FIGS. 3A, 3B, and 3C are diagrams illustrating a sensor device 100 according to an exemplary embodiment.

FIG. 3A shows the construction of a hypothetical sensor device contemplated by the inventors. This sensor device includes a measurement chamber 111 having a biological potential measurement circuit 2, and a plurality of electrode chambers 110 each having an electrode provided therein, these being connected in annular relationship. However, this sensor device does not include an accommodation chamber 112 (e.g., FIGS. 6A, 6B, and 6C) according to the present embodiment as described below.

Figure 3B:
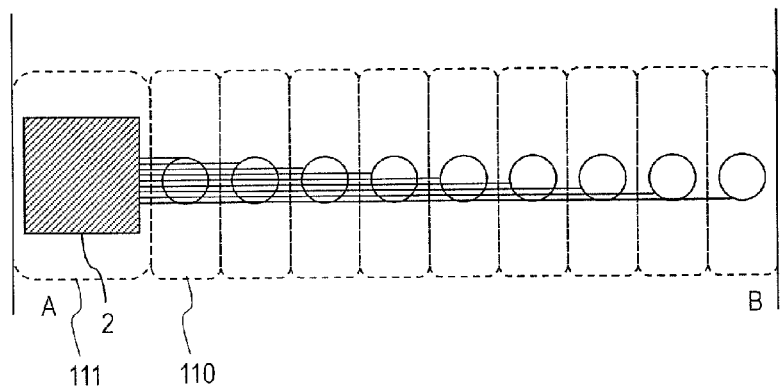
Figure 3C:
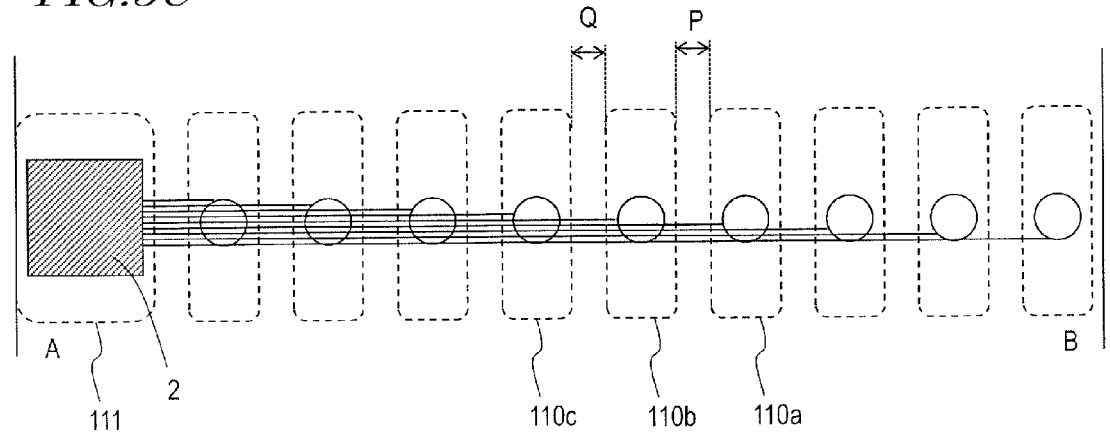

FIGS. 3B and 3C show examples of unfolding the sensor device into a net. Note that the unfolded states shown in FIGS. 3B and 3C illustrate elongation of the sensor device. A and B in FIGS. 3B and 3C correspond to A and B in FIG. 3A. Although the total number of chambers composing the sensor device differs between FIG. 3A and FIGS. 3B and 3C, this is merely for convenience of illustration.

Hereinafter, the forearm will be taken as an example site where the user 1 may wear the sensor device 100. A forearm is the portion of an arm between the elbow and the wrist.

FIG. 3B illustrates an example of unfolding the sensor device, in a situation where a user 1 having thin forearms is wears the sensor device on the forearm. FIG. 3C illustrates an example of unfolding the sensor device, in a situation where a user 1 having thick forearms wears the sensor device on the forearm. Electrically conductive wiring provides interconnection between the biological potential measurement circuit 2 and each electrode chamber 110.

In FIG. 3B, the sensor device has hardly elongated, so that the electrode chambers 110 are in contact with one another at their orifices. In FIG. 3C, in order to adapt to the thickness of the forearm, the interspaces between adjacent electrode chambers are expanded. In other words, depending on the thickness of the forearm of the user who wears it, different internal wiring lengths are needed. The internal wiring is usually metal wiring. It is difficult for the metal wiring which electrically connects the biological potential measurement circuit 2 with the measurement electrodes 113 to expand or contract according to the thickness of the site at which the user 1 wears the sensor. In order to cope with different forearm thicknesses, the metal wiring needs a wiring length which supports the most elongated state of the sensor device.

Assuming that FIG. 3C shows the most elongated state of the sensor device, there are equal distances between adjacent electrode chambers. Specifically, in FIG. 3C, the distance P between adjacent electrode chambers 110a and 110b is equal to the distance Q between adjacent electrode chambers 110b and 110c.

Figures 4, 5:
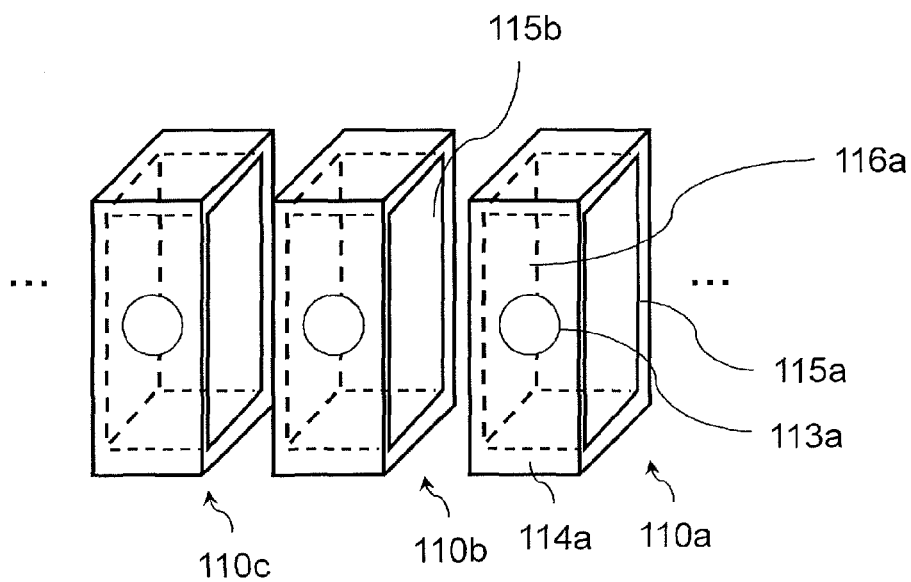
FIG. 4 is a diagram showing individual differences in forearm girth.
FIG. 5 is a diagram showing some of a plurality of electrode chambers 110 according to an exemplary embodiment.

FIG. 4 shows example forearm girths (lengths) of Japanese, according to the AIST human dimensions database 1991-92. It can be seen that about 90% of the forearm girth (length) data, as indicated by the percentile values (mm) in FIG. 4, fall within the range between 210 mm and 280 mm. The inventors believe it desirable that the length of the ring shape (circumferential length) of the sensor device permits adjustment in elongation amounts by at least 70 mm. As a result, the inventors have conceived of the sensor device 100

(FIGS. 2A and 2B) having the accommodation chamber 112, which permits adjustment in elongation amounts of the wiring.

Hereinafter, an example of the sensor device 100 shown in FIG. 2A will be described in detail.

<Sensor Device 100>

As shown in FIGS. 2A and 2B, the sensor device 100 includes the plurality of electrode chambers 110, the measurement chamber 111, and the accommodation chamber 112. In the present embodiment, "chamber" means a construction that is at least partially enclosed by its side faces and yet has an internal space.

The plurality of electrode chambers 110, the measurement chamber 111, and the accommodation chamber 112 become linked with one another to form the annular sensor device 100. In the present embodiment, the internal spaces of the plurality of electrode chambers 110, the internal spaces of the measurement chamber 111, and the internal spaces of the accommodation chamber 112 are contiguous. However, this construction is an example. The internal spaces may not be contiguous; in that case, electrically conductive wiring may extend through connecting portions that interconnect between chambers.

FIG. 5 shows an exemplary construction including three adjacent electrode chambers 110a, 110b, and 110c. The following description will be directed to the construction of the electrode chamber 110a as an example; the same will also apply to the construction of any other electrode chamber.

The electrode chamber 110a includes a measurement electrode 113a.

The electrode chamber 110a has a side face 114a, a first orifice 115a, and a second orifice 116a. On the inside of the electrode chamber 110a, an internal space is created which is contiguous from the first orifice 115a through to the second orifice 116a. One example of the side face 114a of the electrode chamber 110a may be a surface which surrounds the electrode chamber 110a on all sides. Another example of the side face 114a may be a structure which partially surrounds the sides of the electrode chamber 110a. The structure may be rigid or flexible. The same also applies to the measurement chamber 111 and the accommodation chamber 112 described later.

Within the side face 114a of the electrode chamber 110a, the measurement electrode 113a is disposed on a surface (inner peripheral surface) which lies on the inside of the ring shape of the sensor device 100 that is created by the plurality of electrode chambers 110 and the like. The inner peripheral surface is a surface which comes in contact with the skin of the user 1 wearing the sensor device 100 on his or her forearm. As shown in FIG. 2C, as the user 1 wears the sensor device 100, the measurement electrode 113a comes in contact with the user 1.

Next, relative positioning of the plurality of electrode chambers 110 shown in FIG. 5 will be described. The electrode chamber 110a and the electrode chamber 110b are taken as an example. The electrode chamber 110a and the electrode chamber 110b are placed so that the orifice 116a of the electrode chamber 110a lies opposite to the orifice 115b of the electrode chamber 110b. For example, electrically conductive wiring which connects the measurement electrode 113a and the biological potential measurement circuit 2 is provided so as to pass through the orifice 116a and the orifice 116b.

Next, the measurement chamber 111 will be described.

Figure 6A:
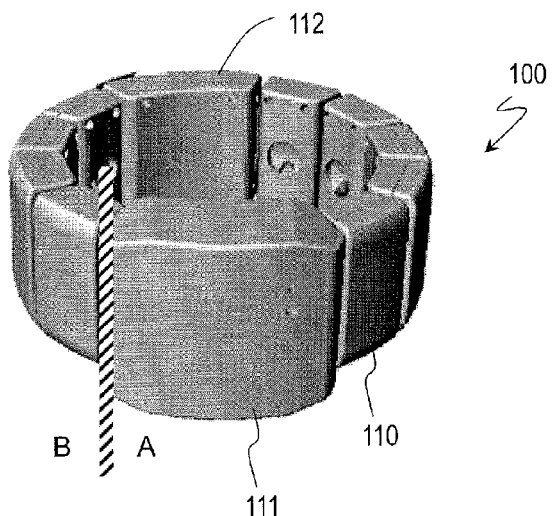
FIGS. 6A, 6B, and 6C are diagrams illustrating a sensor device 100 according to an exemplary embodiment.
Figure 6B:
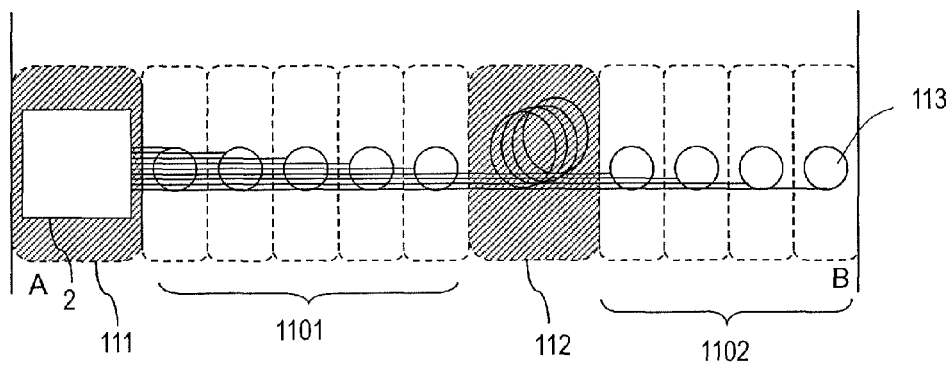
Figure 6C:
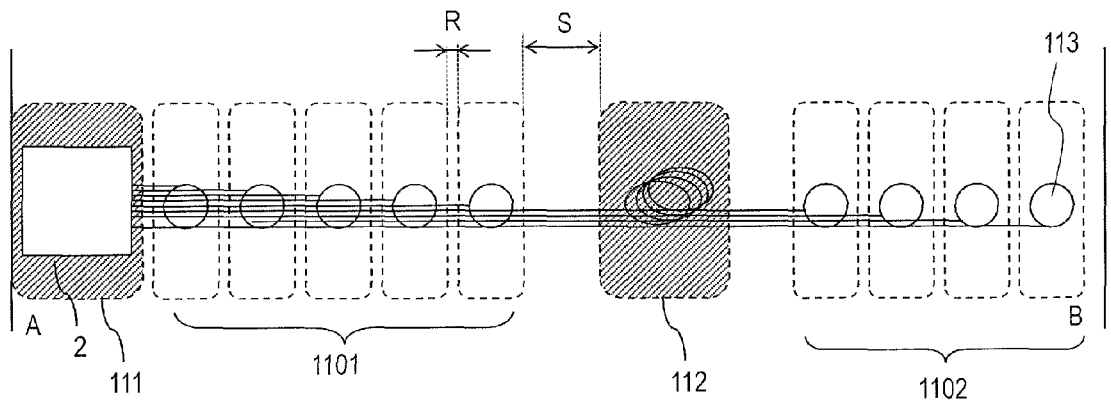

The measurement chamber 111 includes the biological potential measurement circuit 2 in its interior. FIG. 6A illustrates the sensor device 100 of the present embodiment and unfolding positions A and B. FIGS. 6B and 6C show examples of unfolding the sensor device 100 at unfolding positions A and B. FIGS. 6B and 6C depict the biological potential measurement circuit 2 included in the measurement chamber 111. The biological potential measurement circuit 2 is electrically connected to the measurement electrodes 113 via metal wiring.

The measurement chamber 111 may include a ground electrode and a reference electrode, in which case the biological potential measurement circuit 2 is electrically connected to the ground electrode and the reference electrode.

The biological potential measurement circuit 2 measures the biological potential of the user 1 by using the measurement electrodes 113 of the respective electrode chambers.

The annular sensor device 100 is constructed by connecting the plurality of electrode chambers 110, the measurement chamber 111, and the accommodation chamber 112 in order. In the present embodiment, the internal spaces of the plurality of electrode chambers 110, the internal space of the measurement chamber 111, and the internal space of the accommodation chamber 112 are contiguous.

In order to measure the biological potential of the user 1, it is desirable to increase the intensity of contact (closeness of contact) between the user 1 and the measurement electrodes 113 to reduce contact impedance. Therefore, it is desirable that, while the user 1 is wearing the sensor device 100, the site of the body of the user 1 at which the sensor device 100 is worn has a similar size to that of the ring of the ring-shaped sensor device 100. This provides improved contact between the user 1 and the measurement electrodes 113.

Moreover, for example, there may be a case where the sensor device 100 is constructed so that the plurality of electrode chambers 110, the measurement chamber 111, and the accommodation chamber 112 cannot be disconnected from one another. For example, the plurality of electrode chambers 110, the measurement chamber 111, and the accommodation chamber 112 may be connected by a connection line which penetrates through the internal spaces of the plurality of electrode chambers 110, the internal space of the measurement chamber 111, and the internal space of the accommodation chamber 112. The connection line is made of an elastic member. Examples of the connection line are rubbers, including natural rubbers, synthetic rubbers, etc.

In this case, when the user 1 wears the sensor device 100 on a forearm, the user 1 will pass the sensor device 100 from the tip of the hand onto the back and so on, until finally wearing it on the forearm. Therefore, it is desirable that the metal wiring of the sensor device 100 has a size which supports not only the thickness of the site at which the user 1 wears the sensor device 100, but also the size of any site of the user 1 which will be passed through when the sensor device 100 becomes worn.

By having the accommodation chamber 112, the sensor device 100 of the present disclosure implements metal wiring that supports elasticity. The net illustrations of FIGS. 6B and 6C also depict the accommodation chamber 112.

As shown in FIGS. 6A, 6B, and 6C, the accommodation chamber 112 is provided between plural electrode chambers 110. The order in which they are arranged is, as shown in FIGS. 6B and 6C: the measurement chamber 111, the plurality of electrode chambers 110 (also referred to as the first electrode chamber group 1101), the accommodation chamber 112, and then the plurality of electrode chambers 110 (also referred to the second electrode chamber group 1102). The accommodation chamber 112 does not include a measurement electrode because the accommodation chamber 112 is positioned so as to come in contact with a site where there are relatively few muscles upon attachment on the forearm of the user 1. The details of the arrangement will be described later.

Figure 7A:
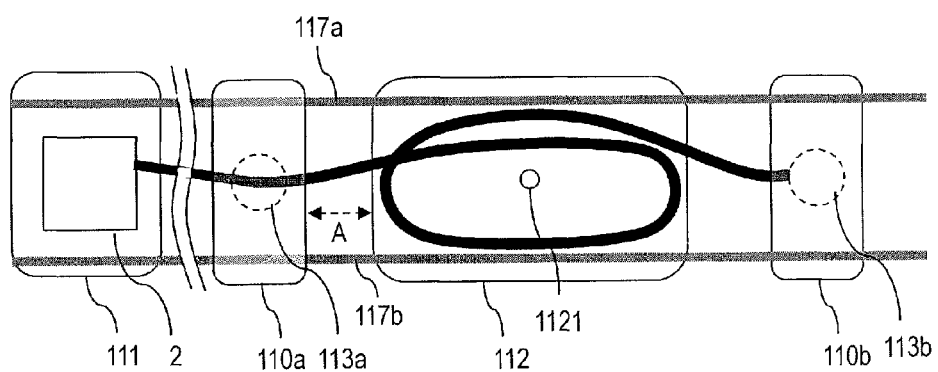
FIGS. 7A and 7B are partially enlarged views of the sensor device 100 according to an exemplary embodiment.
Figure 7B:
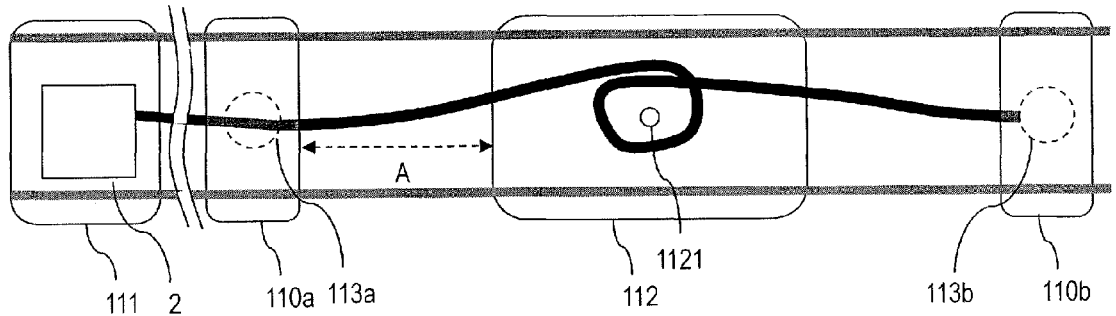

The accommodation chamber 112 accommodates the metal wiring which connects the biological potential measurement circuit 2 and the measurement electrodes of the chambers belonging to the second electrode chamber group 1102. The accommodation chamber 112 has a protrusion on the inside. For example, FIGS. 7A and 7B show partially enlarge views of the sensor device 100 as viewed from the inside of the ring shape which is constituted by the sensor device 100. It can be seen that the accommodation chamber 112 has a protrusion 1121. The metal wiring extending from the biological potential measurement circuit 2 makes a circle around the protrusion 1121 of the accommodation chamber 112, so as to be contiguous with the measurement electrodes. The metal wiring which connects the measurement electrodes 113 and the biological potential measurement circuit 2 extends around the protrusion 1121, with a length which enables longitudinal feeding in accordance with the amount of elongation when the sensor device 100 becomes elongated.

Note that FIGS. 7A and 7B only show the electrode chambers 110a and 110b, while omitting some of the plurality of electrode chambers 110. Also, FIGS. 7A and 7B only show the metal wiring which electrically connects the biological potential measurement circuit 2 included in the measurement chamber 111 and the measurement electrode 113b located on the electrode chamber 110b, while omitting some of the metal wiring which is contained in the sensor device 100.

The protrusion of the accommodation chamber 112 may be in a columnar shape which abuts with a first side face of the internal space of the accommodation chamber 112 and a second side face opposing the first side face. Alternatively, the protrusion may have a predetermined height or greater from the first side face of the internal space of the accommodation chamber 112. For example, an example height of the protrusion may be a height that allows all metal wiring that extends from the biological potential measurement circuit 2 to the measurement electrodes 113 of the second electrode chamber group 1102 to be caught by the protrusion.

See FIGS. 6A, 6B, and 6C again. The examples of unfolding in FIGS. 6B and 6C are shown in a manner of illustrating elongations of the sensor device 100 when a user 1 having thin forearms and a user 1 having thick forearms wear the sensor device 100.

In a comparison between the example of FIG. 6B and the example of FIG. 6C, longer metal wiring length is fed out in the example of FIG. 6C, because of the sensor device 100 being elongated. Stated otherwise, the wiring length remaining inside the accommodation chamber 112 is longer in the example of FIG. 6B. Thus, according to the present embodiment, the ring diameter of the ring shape of the sensor device 100 can be varied by changing the length of the metal wiring that is situated in the accommodation chamber 112, thereby being able to adapt to the thickness of the site at which the sensor device 100 is worn by the user 1. Specifically, as shown in FIGS. 6B and 6C, without requiring the metal wiring itself to expand or contract, the length of the metal wiring situated inside the accommodation chamber 112 allows for adjustment of the length between the first electrode chamber group 1101 and second electrode chamber group 1102 and the accommodation chamber 112.

Assuming that FIG. 6C shows the most elongated state of the sensor device, the distance between any two adjacent electrode chambers is different from the distance between an electrode chamber and the accommodation chamber 112. Specifically, in FIG. 6C, the distance R between adjacent electrode chambers and the distance S between the accommodation chamber 112 and an adjacent one of the electrode chambers are of the relationship R<S.

This allows the electrodes to be concentrated in areas around the arm that are equipped with more muscles. Agonist muscles and antagonist muscles for making arm motions are concentrated in opposing areas, thus resulting in areas with more muscles and areas with fewer muscles. The aforementioned electrode arrangement corresponds to such muscle positions, thus being effective for acquiring myoelectric signals.

Next, see FIGS. 7A and 7B.

The measurement chamber 111, the electrode chamber 110a, the accommodation chamber 112, and the electrode chamber 110b are connected by connection lines 117a and 117b.

The metal wiring shown in FIGS. 7A and 7B extends so as to make at least one round around the protrusion 1121 of the accommodation chamber 112, thus connecting the biological potential measurement circuit 2 with the measurement electrode 113b. Note that the metal wiring extending around the protrusion 1121 has a wiring length sufficiently longer than the length of the circumference of the protrusion 1121, thus being longer than a length which enables longitudinal feeding when the sensor device is most elongated.

The distance between the electrode chamber 110a and the accommodation chamber 112 shown in FIG. 7B is greater than the distance between the electrode chamber 110a and the accommodation chamber 112 shown in FIG. 7A. This difference in distance corresponds to the difference in diameter of the ring shapes that are created by the sensor device 100 when worn by users with different forearm thicknesses.

In FIG. 7A, the metal wiring broadly or loosely wraps around the protrusion of the accommodation chamber 112, with increased length of metal wiring situated inside the accommodation chamber 112, thus decreasing the diameter of the ring shape created by the sensor device 100. On the other hand, in FIG. 7B, the metal wiring wraps around the protrusion of the accommodation chamber 112, in a manner of achieving contact between the metal wiring and the accommodation chamber 112, thus resulting in decreased length of metal wiring situated inside the accommodation chamber 112 and increasing the diameter of the ring shape created by the sensor device 100.

Thus, the metal wiring is disposed so as to make a circle around the protrusion 1121 of the accommodation chamber 112, so that the diameter of the ring shape of the sensor device 100 can be altered without requiring the metal wiring itself to expand or contract.

Next, details concerning attachment of the sensor device 100 will be described.

A case will be considered where the sensor device 100 is worn on an arm of the user 1 in order to measure myoelectric potential, as shown in FIG. 2C, for example. Assume however that the user 1 has his or her right-hand palm turned upward. In this case, the surface of the palm of the user 1 (hereinafter also referred to as the "arm upper (i.e., anterior) face") is in contact with the measurement chamber 111, and the surface of the back of the hand of the user 1 (hereinafter also referred to as the "arm lower (i.e., posterior) face") is in contact with the accommodation chamber 112.

The user's arm muscles (mainly with regard to extensor muscles) are located in the arm upper face and arm side faces. Arm side faces are the surfaces located between the arm upper face and the arm lower face. Arm side faces include an inner side face which is located on the little-finger side of the palm of the user 1 and an outer side face which is located on the thumb side.

In order to acquire myoelectric potential of the user, it is desirable that the measurement electrodes 113 of the sensor device 100 are located in contact with the arm upper face and the arm side face(s). In particular, it is desirable that the measurement electrodes 113 are located in contact with portions where the user's muscles will undergo large motions.

Since the arm lower face has relatively few muscles as compared to other portions, there is little significance in providing the measurement electrodes 113 there. Therefore, the measurement chamber 111, which lacks a measurement electrode 113, is positioned so that the measurement chamber 111 will come in contact with the arm lower face. In the case where the measurement chamber 111 has a reference electrode or a ground electrode, it is desirable to arrange the measurement chamber 111 so that the measurement chamber 111 will come in contact with the arm upper face. The reason is that the arm upper face is relatively flat, thus facilitating contact between the reference electrode or ground electrode with the user 1. In this context, it is desirable that the length of the measurement chamber 111 is greater than the length of the electrode chamber 110 along the circumferential direction of the ring created by the sensor device 100, so that the reference electrode or ground electrode of the measurement chamber 111 can easily come in contact with the user 1, in which case it is easy to set criteria for myoelectric potential measurement.

Moreover, bones are located at the arm lower face of the user, possibly making it difficult to achieve close contact between the measurement electrodes 113 and the arm lower face. In particular, bone protrusions exist near the elbow, possibly making it difficult to achieve contact between the electrodes and the arm. Therefore, the accommodation chamber 112 lacking a measurement electrode 113 is positioned so as to come in contact with the arm lower face of the user.

The accommodation chamber 112 and the measurement chamber 111 are placed in opposite positions sandwiching the electrode chamber 110. Conceivably, the flat portion of the arm upper face and the bones in the arm lower face may not be in completely opposite positions. As shown in FIG. 2A, rather than at symmetric positions with respect to the center of the ring shape of the sensor device 100, the accommodation chamber 112 and the measurement chamber 111 may be placed in asymmetric positions which are deviated by a predetermined distance or less from the symmetric positions, in accordance with the shape of the user's arm. Such deployment at asymmetric positions deviated by a predetermined distance or less from the symmetric positions in accordance with the shape of the user's arm is also meant to fall under the definition of the accommodation chamber 112 and the measurement chamber 111 being opposite from each other.

<Biological Potential Input Interface System 1000>

Figure 8:
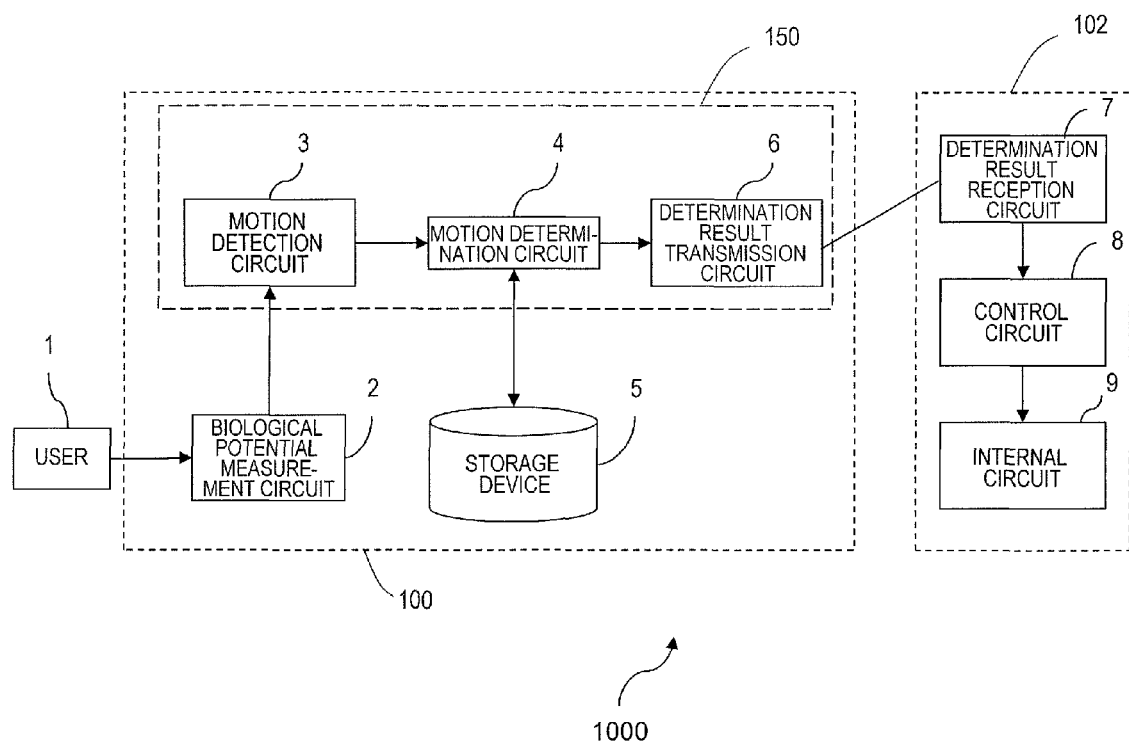
FIG. 8 is a diagram showing an exemplary construction of a biological potential input interface system 1000 according to an exemplary embodiment.

FIG. 8 shows an exemplary construction of the interface system 1000. The interface system 1000 shown in FIG. 8 includes the sensor device 100 and the appliance 102.

In the exemplary construction of FIG. 8, the sensor device 100 recognizes a gesture of the user 1, and sends a control signal for controlling the appliance 102.

The sensor device 100 includes the biological potential measurement circuit 2, a storage device 5, and a determination circuit 150.

The determination circuit 150 includes a motion detection circuit 3, a motion determination circuit 4, and a determination result transmission circuit 6. Hereinafter, an operation of the sensor device 100 will be described with reference also to the constituent elements of the determination circuit 150.

Note that the determination circuit 150 may be implemented by the hardware which composes a signal processing section 220, described later (FIG. 9): a CPU, a RAM, a computer program, and a ROM, for example. The aforementioned motion detection circuit 3, motion determination circuit 4, and determination result transmission circuit 6 are functions of the CPU which are realized as the CPU lays out a computer program stored in the ROM onto the RAM and executes it. At each given point in time, the CPU operates as the motion detection circuit 3, the motion determination circuit 4, and/or the determination result transmission circuit 6. Note that the determination circuit 150 may be composed of one or more calculation circuits (Digital Signal Processors: DSPs).

The appliance 102 includes a determination result reception circuit 7, a control circuit 8, and an internal circuit 9. The sensor device 100 and the appliance 102 are connected in a wired or wireless manner for exchanging information therebetween.

<Sensor Device 100>

Using the plurality of electrically connected measurement electrodes, the biological potential measurement circuit 2 measures biological potential of the user 1. An example of biological potential of the user 1 is myoelectric potential. Against a prestored detection criterion, the motion detection circuit 3 detects a number of biological potentials corresponding to an intentional motion (gesture) of the user 1, from among a plurality of biological potentials which are measured by the biological potential measurement circuit 2. For example, the motion detection circuit 3 retains a predetermined threshold voltage value as a detection criterion, and detects any potential which is equal to or greater than the predetermined threshold value from among the biological potentials measured by the biological potential measurement circuit 2. Alternatively, as the detection criterion, a myoelectric potential that corresponds to a predetermined motion of the user is prestored. If the degree of matching between a measured biological potential and the prestored myoelectric potential is equal to or greater than a predetermined threshold value, then the measured biological potential is detected as an intentional motion. The motion detection circuit 3 prestores the predetermined threshold value for degree-of-matching determination. Myoelectric potential corresponding to a predetermined motion refers to magnitude information of the potentials of the respective measurement electrodes. Magnitudes of the potentials of the respective measurement electrodes may be in absolute values, or a proportional expression of potential magnitude may be used.

Referring to a determination criterion which is retained in the storage device 5, the motion determination circuit 4 determines a gesture which corresponds to the measured biological potential. The motion determination circuit 4 may determine a gesture corresponding to the biological potential when the motion detection circuit 3 has detected an intentional motion of the user.

The storage device 5 retains a determination criterion which defines associations between potentials and motions (gestures), this determination criterion having been prepared in advance. An example criterion is information which defines associations between motions (gestures) and the magnitudes of potentials that were measured by the manufacturer of the sensor device 100 by using the respective measurement electrodes during design of the sensor device 100. Magnitudes of the potentials of the respective measurement electrodes may be in absolute values, or a proportional expression of potential magnitude may be used.

To the appliance 102, the determination result transmission circuit 6 sends a control signal for realizing an operation of the appliance 102 that corresponds to the gesture which has been determined by the motion determination circuit 4.

Note that the motion determination circuit 4 may acquire a determination criterion in a wired or wireless manner from a storage device 5 which is external to the sensor device 100, and determine a motion based on this acquired determination criterion. In other words, the sensor device 100 may not include the storage device 5. Similarly, the motion detection circuit 3 may acquire a detection criterion from an external storage, and perform detection based on the acquired detection criterion.

<Appliance 102>

The determination result reception circuit 7 is a communications circuit. The determination result reception circuit 7 communicates with the determination result transmission circuit 6 by using the same communications method as that of the determination result transmission circuit 6. From the sensor device 100 (determination result transmission circuit 6), the determination result reception circuit 7 receives a control signal for realizing an operation of the appliance 102 that corresponds to the gesture of the user 1.

By referring to prestored manipulation references, the control circuit 8 determines a manipulation that corresponds to the gesture of the user 1. Based on the determined manipulation, the control circuit 8 controls the operation of the internal circuit 9 of the appliance 102. The internal circuit 9 is a circuit which realizes the functions of the appliance 102. For example, if the appliance is a television set, the internal circuit 9 is at least one of a video/audio signal reception circuit, a decoding circuit, a signal processing circuit, and a video/audio output circuit. If the gesture of the user 1 corresponds to a channel switching operation, based on a control signal for channel switching, the control circuit 8 controls a video/audio signal reception circuit which is the internal circuit 9, and selects a data stream for decoding from within the broadcast wave of a digital broadcast.

<Hardware Construction of the Sensor Device 100>

Figure 9:
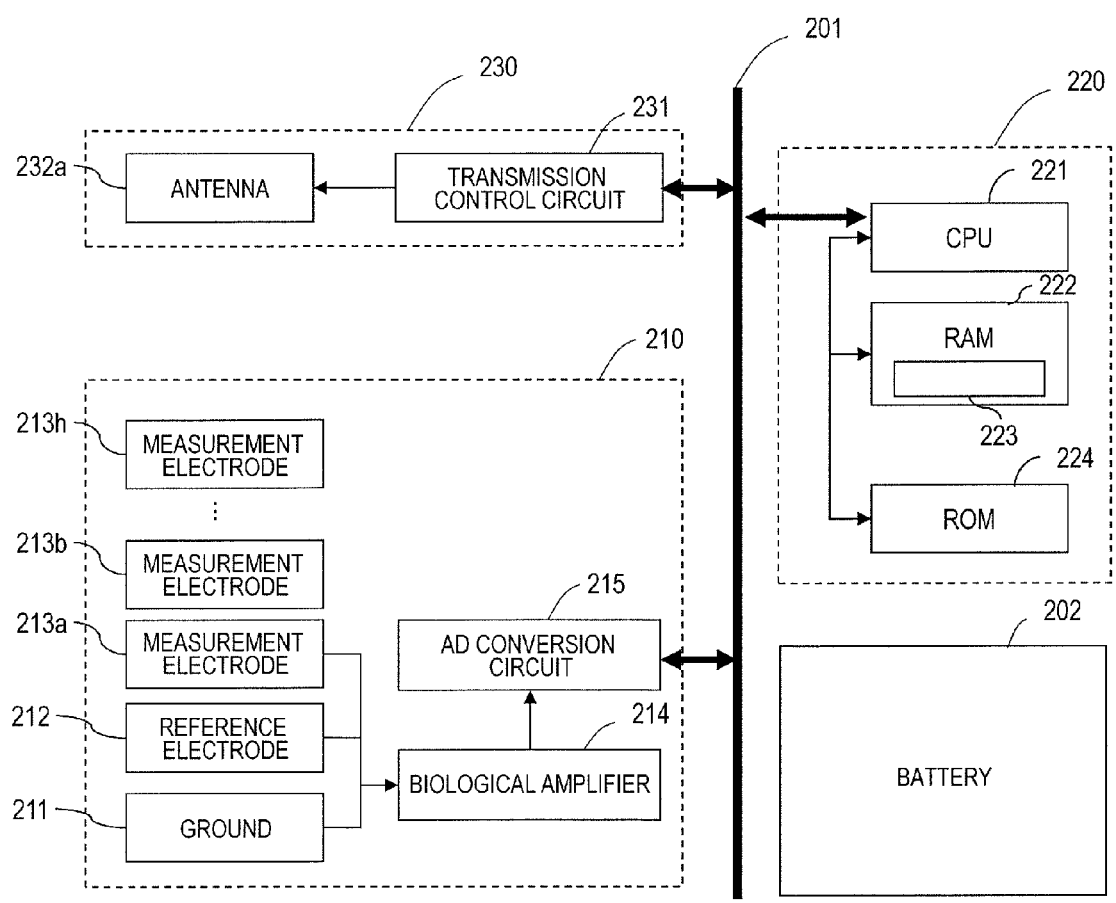
FIG. 9 is a diagram showing the hardware construction of the sensor device 100 according to an exemplary embodiment.

FIG. 9 shows the hardware construction of the sensor device 100 shown in FIG. 8.

The sensor device 100 includes a plurality of functional blocks. The sensor device 100 includes a biological potential measurement circuit 210, a signal processing section 220, a transmission circuit 230, and a battery 202. The biological potential measurement circuit 210, the signal processing section 220, and the transmission circuit 230 are connected via a bus 201.

The biological potential measurement circuit 210 corresponds to the biological potential measurement circuit 2, the measurement electrodes 113, a reference electrode, and a ground electrode. The biological potential measurement circuit 210 includes ground 211, a reference electrode 212, measurement electrodes 213a to 213h, a biological amplifier 214, and an AD conversion circuit 215. In the biological amplifier 214, the biological potential measurement circuit 210 amplifies a potential which has been measured with the ground 211, the reference electrode 212, and the measurement electrodes 213a to 213h. The AD conversion circuit 215 converts the potential (analog signal) which has been amplified by the biological amplifier 214 into a digital signal.

The signal processing section 220 includes a CPU (central processing unit, or signal processor) 221, a RAM 222, a computer program 223, and a ROM 224. The computer program 223 is stored in the ROM 224, for example, and read from the ROM 224 so as to be laid out on the RAM 222. The signal processing section 220 corresponds to the motion detection circuit 3, the motion determination circuit 4, and the storage device 5.

The transmission circuit 230 includes an antenna 232a and a transmission control circuit 231. The transmission circuit 230 corresponds to the determination result transmission circuit 6. For example, the battery 202 includes a lithium ion battery and a charge/discharge control circuit which are not shown.

<Processes by the Biological Potential Input Interface System 1000>

Figure 10:
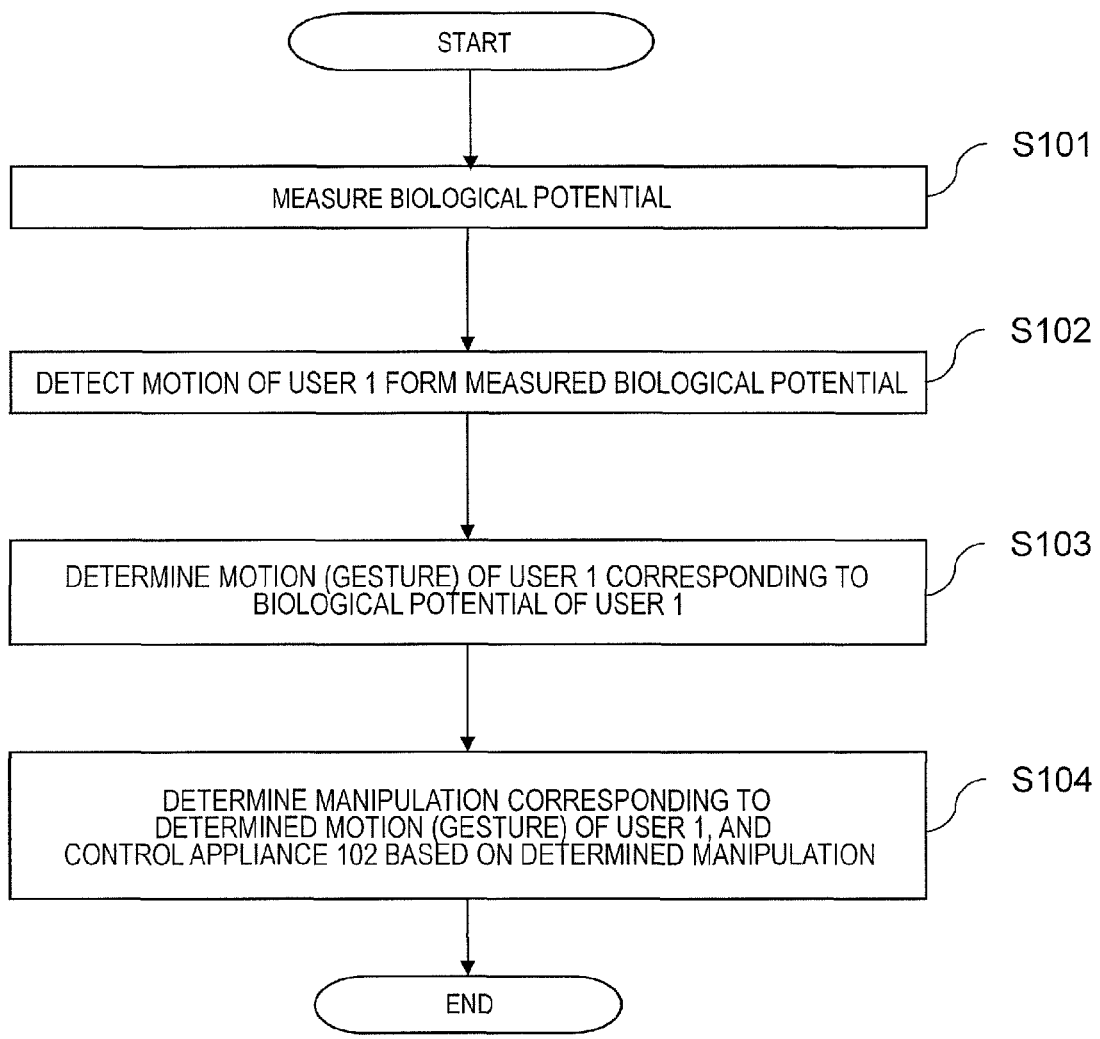
FIG. 10 is a flowchart of processes by the biological potential input interface system 1000 according to an exemplary embodiment.

FIG. 10 shows a flowchart of processes by the interface system 1000. An example where, as shown in FIG. 2C, the sensor device 100 is worn on a forearm of the user 1 will be described.

At step S101, the biological potential measurement circuit 2 measures biological potential of the user 1 by using the plurality of measurement electrodes. In the present embodiment, biological potential means myoelectric potential of a forearm of the user 1.

Figure 11:
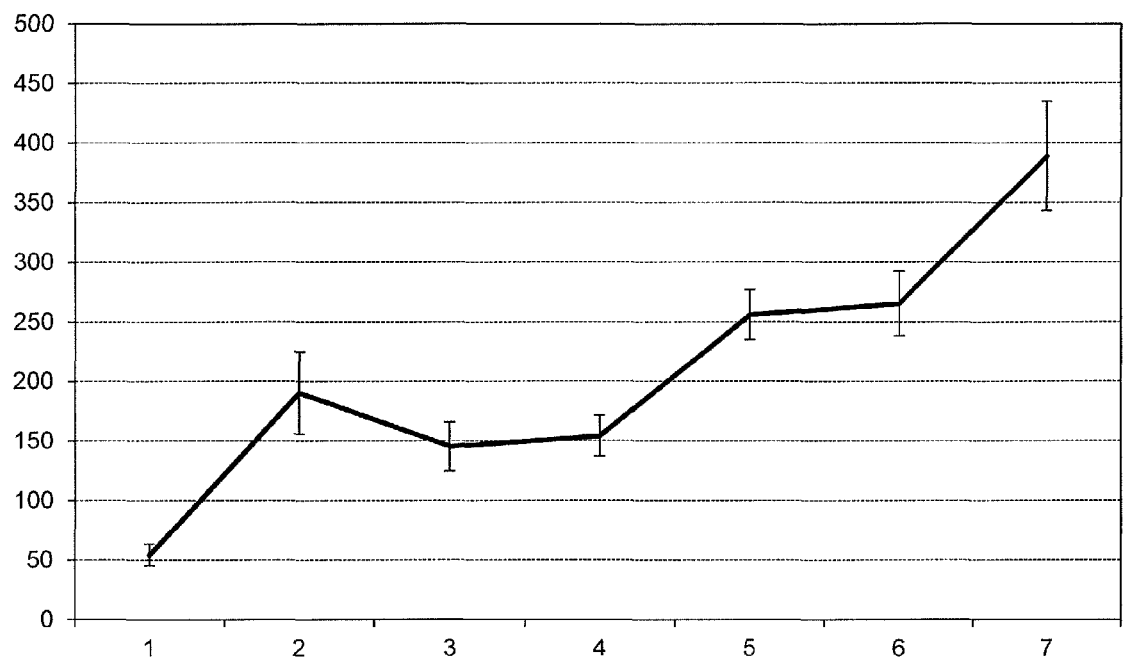
FIG. 11 is a diagram showing examples of measured myoelectric potential according to an exemplary embodiment.

FIG. 11 shows example myoelectric potentials which are measured by the biological potential measurement circuit 2. In FIG. 11, the vertical axis represents potential magnitude ($\mu V$), and numbers on the horizontal axis denote the respective measurement electrodes. The example myoelectric potentials shown in FIG. 11 were measured in the biological potential measurement circuit 2 by using eight measurement electrodes. Potentials 1 to 7 indicated on the horizontal axis represent potentials which were measured in the biological potential measurement circuit 2 by, while assigning one of the eight measurement electrodes as a reference electrode, respectively using the other first to seventh measurement electrodes against the reference electrode. Hereinafter, potentials 1 to 7 shown in FIG. 11 may also be denoted as channels 1 to 7.

At step S102, the motion detection circuit 3 detects a biological potential (myoelectric potential) of the user 1 which is equal to or greater than a predetermined threshold value. The predetermined threshold value is the magnitude of a potential which is greater than the potential of any motion at normal times and yet fits within the potential range corresponding to intentional motions of the user 1. The predetermined threshold value can be set based on previously measured potentials, in accordance with the site at which the user 1 wears the sensor device 100 or with the user 1 who wears the sensor device 100.

For example, the motion detection circuit 3 acquires a point in time at which at least one myoelectric potential of the measured plurality of myoelectric potentials was equal to or greater than the predetermined threshold value. The acquired point in time may have some span. With regard to the acquired point in time, the myoelectric potential pattern which was measured by the biological potential measurement circuit 2 is determined as a biological potential pattern that corresponds to the motion (gesture) of the user 1.

In the example shown in FIG. 11, if the predetermined threshold value is a potential that reads 200 on the vertical axis, the potentials of channels 5 to 7 exceed the threshold value. Therefore, the motion detection circuit 3 determines the potentials of channels 1 to 7 at the point in time associated with potentials exceeding the threshold value as the biological potential pattern corresponding to the intentional motion (gesture) of the user 1.

If the motion detection circuit 3 fails to detect a biological potential corresponding to an intentional motion of the user 1, the process returns to step S101. If the motion detection circuit 3 detects a biological potential pattern corresponding to an intentional motion of the user 1, the process proceeds to step S103.

Figure 12:
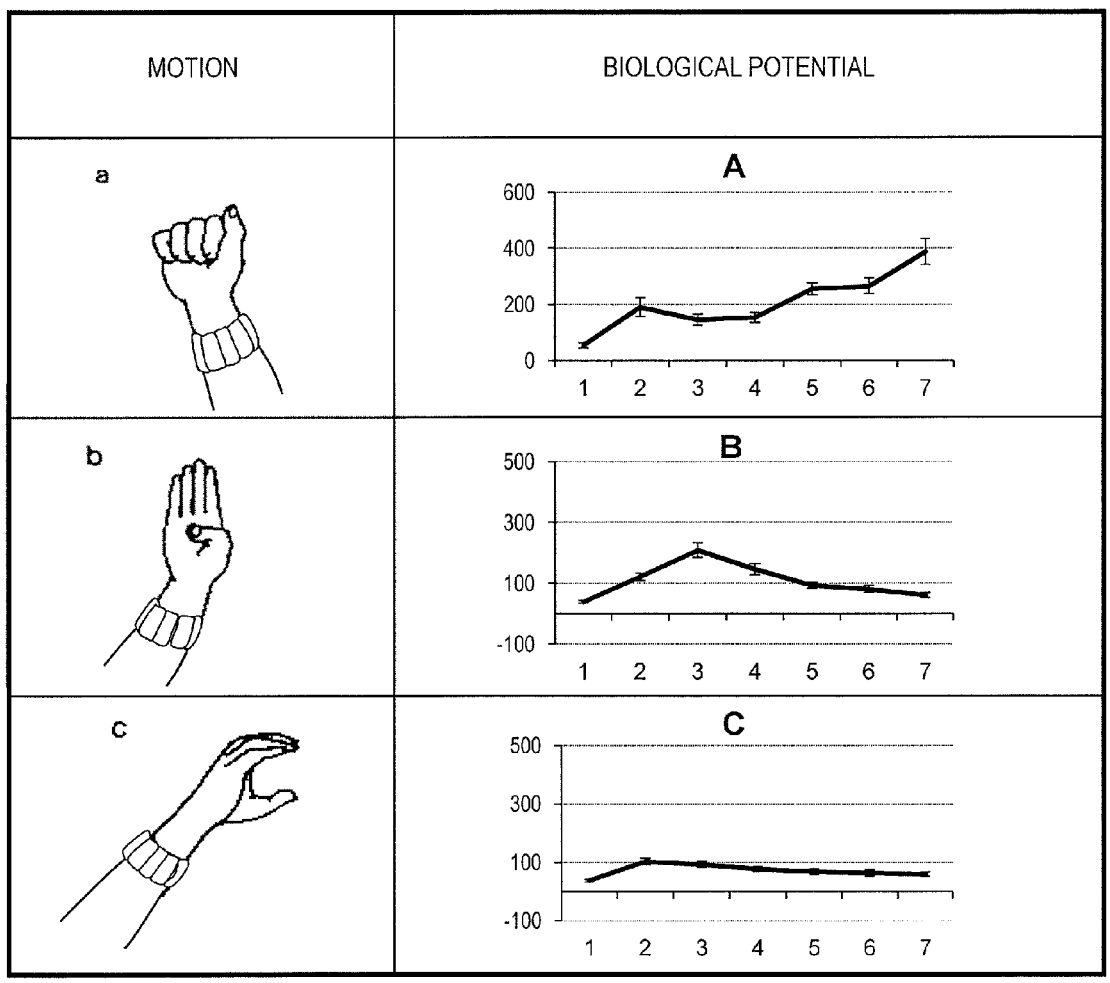
FIG. 12 is a diagram of references stored in a storage device 5 according to an exemplary embodiment.

At step S103, against the references retained in the storage device 5, the motion determination circuit 4 detects a motion that corresponds to the biological potential pattern which has been detected by the motion detection circuit 3. FIG. 12 shows an example of information which defines associations between motions and biological potentials that is stored in the storage device 5. FIG. 12 shows hand motions, e.g., a motion of gripping a hand into a first ("stone"), opening the hand with the thumb being bent, and so on, together with potential magnitudes on the respective channels.

For example, against the references stored in the storage device 5 as shown in FIG. 12, the motion determination circuit 4 determines a motion that corresponds to the potential pattern of FIG. 11 which has been detected by the motion detection circuit 3. In this case, the motion determination circuit 4 determines that the potential pattern shown in FIG. 11 corresponds to motion a.

The determination result transmission circuit 6 sends the motion which has been determined by the motion determination circuit 4 to the appliance 102.

At step S104, the determination result reception circuit 7 receives from the determination result transmission circuit 6 a control signal concerning the motion which has been determined by the motion determination circuit 4.

Against prestored manipulation references, the control circuit 8 determines a manipulation that corresponds to the gesture of the user 1. Based on the determined manipulation, the control circuits 8 controls manipulation of the internal circuit 9.

Figure 13:
FIG. 13 is a diagram showing examples of manipulation references prestored in a control circuit 8 according to an exemplary embodiment.
Figure 13:
Figure 13:
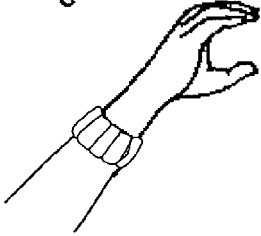

FIG. 13 shows examples of manipulation references which are prestored in the control circuit 8. The example shown in FIG. 13 is information in which motions are associated with manipulations of the appliance 102. Example manipulations of the appliance 102 include powering ON or OFF of the appliance 102, sound volume adjustment (increasing or decreasing the sound volume), and execution of an operation which has been set (forward, backward, zoom in, zoom out, etc.).

<Variant 1 of the Flow of Processes in FIG. 10>

At step S102, the motion determination circuit 4 may make its determination by using a myoelectric potential pattern after a predetermined time since the acquired point in time as the biological potential pattern corresponding to the motion (gesture) of the user 1. The predetermined time is to be prestored in the storage included in the motion detection circuit 3.

Alternatively, the motion determination circuit 4 may previously retain the predetermined time, acquire a point in time from the motion detection circuit 3, and thus acquire a relevant biological potential pattern to the motion for determination.

In this context, the intentional motion (also referred to as the first motion) which is detected by the motion detection circuit 3 and the motion (also referred to as the second motion) determined at step S103 by the motion determination circuit 4 would be different. The user 1 would be making a first motion for causing the processing by the biological potential input interface to begin, and a second motion as a manipulation input for the appliance 102.

<Variant 2 of the Flow of Processes in FIG. 10>

In the example shown in FIG. 10, the interface system 1000 determines a manipulation for the device to be controlled from the biological potential of the user 1, by using the references in FIG. 12 and FIG. 13.

Figure 14:
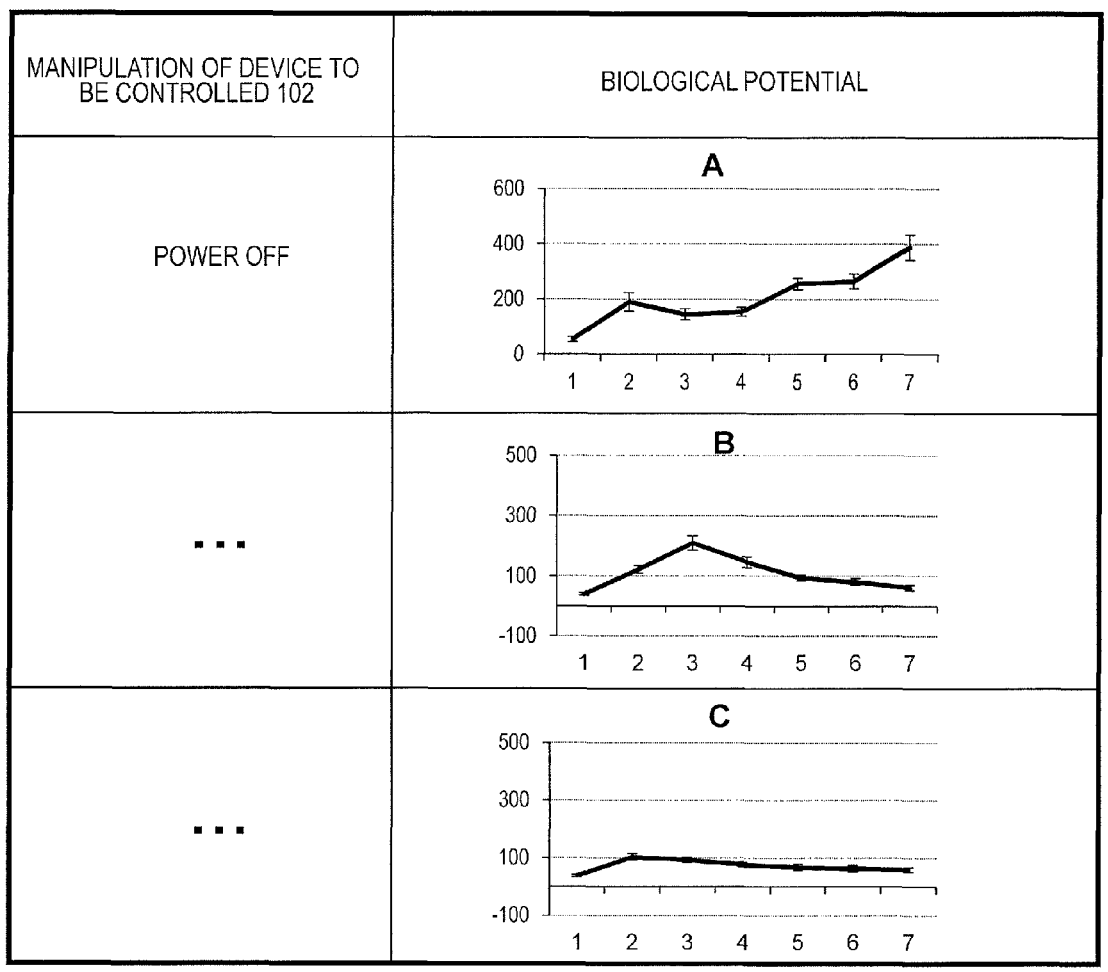
FIG. 14 is a diagram showing information which defines associations between user biological potentials and manipulations of the appliance 102 according to an exemplary embodiment.

FIG. 14 shows an example of information which defines associations between user biological potentials and manipulations of the appliance 102.

This information may be retained in the storage device 5, for example. By referring to the information which defines associations between user biological potentials and manipulations of the appliance 102, the motion determination circuit 4 determines a manipulation for the appliance 102 from the user biological potential. The sensor device 100 (determination result transmission circuit 6) sends this manipulation for the appliance 102 to the appliance 102.

Based on the manipulation for the appliance 102 as received from the sensor device 100, the control circuit 8 controls the manipulation of the device to be controlled.

<Variant 1 of the Biological Potential Input Interface System>

Figure 15:
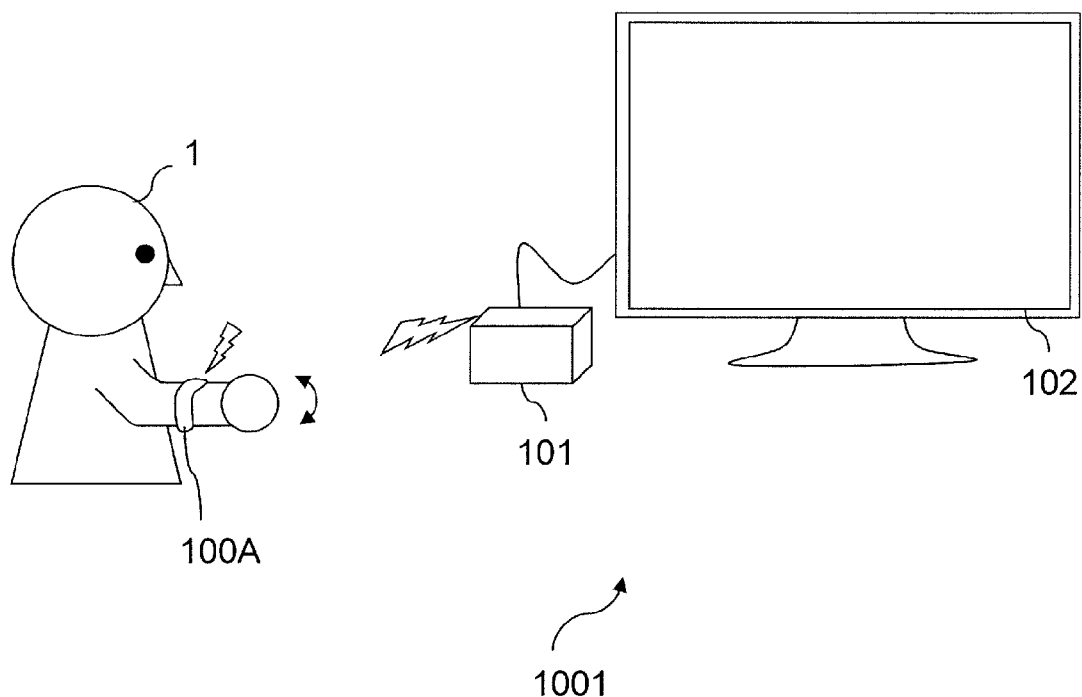
FIG. 15 is a diagram showing the construction of a variant biological potential input interface system 1001 according to an exemplary embodiment.

FIG. 15 shows the construction of a biological potential input interface system 1001. The biological potential input interface system 1001 is a variant of the interface system 1000 shown in FIG. 1. The interface system 1001 additionally includes a recognition device 101, which performs some of the functions of the sensor device 100 shown in FIG. 1. Consequently, the interface system 1001 utilizes a sensor device 100A which is simpler in construction than the sensor device 100.

Figure 16:
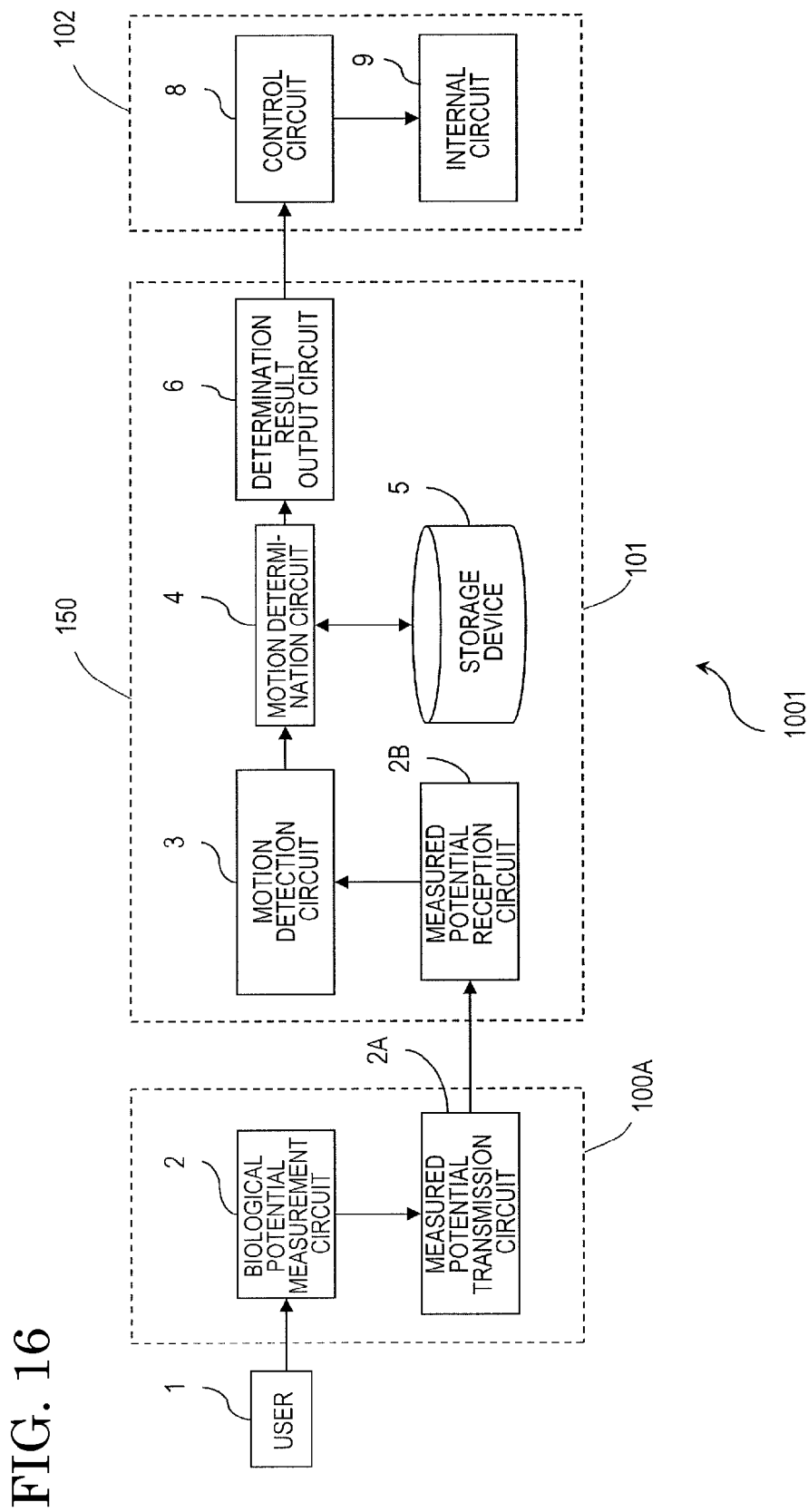
FIG. 16 is a diagram showing the construction of the biological potential input interface system 1001 according to an exemplary embodiment.

FIG. 16 shows the construction of the biological potential input interface system 1001. The biological potential input interface system 1001 shown in FIG. 16 includes a sensor device 100A, a recognition device 101, and an appliance 102. The sensor device 100A, the recognition device 101, and the appliance 102 are connected in a wired or wireless manner for exchanging information therebetween.

One specific difference of the interface system 1001 according to the present variant from the interface system 1000 (FIG. 1) is that the storage device 5 and the determination circuit 150 are provided in the recognition device 101, rather than in the sensor device 100.

The sensor device 100A includes the biological potential measurement circuit 2 and a measured potential transmission circuit 2A. The recognition device 101 includes a measured potential reception circuit 2B, the motion detection circuit 3, the motion determination circuit 4, the storage device 5, and the determination result transmission circuit 6. The appliance 102 includes the control circuit 8 and the internal circuit 9.

The measured potential transmission circuit 2A included in the sensor device 100A sends measured biological potential to the measured potential reception circuit 2B included in the recognition device 101.

The biological potential input interface system 1001 shown in FIG. 16 performs processes similar to those of the flowchart shown in FIG. 10.

According to the present disclosure, variations in terms of differing forearm thickness from individual to individual are absorbed at two points, i.e., the sensor module and the cable accommodating circuit. Thus, more electrodes can be concentrated in areas of the agonist muscles and antagonist muscles which are used for expressing gestures, thereby enabling size adaptation while ensuring accuracy. This mechanism of size adaptation is broadly applicable to situations where information is to be expressed by hand gestures. Specifically, it is applicable to not only manipulations of television sets, but also manipulations of household appliances, peripheral devices during hospitalization, or smartphones, etc., to be performed with the biological potential input interface worn on a forearm.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A biological potential input interface system comprising:
   a sensor device configured to measure biological potential of a user;
   a determination circuit configured to determine a motion of the user from the biological potential of the user against a determination criterion which is prepared in advance, and generate a control signal corresponding to the motion; and
   a control circuit configured to control operation of an internal circuit of an appliance based on the control signal,
   wherein the sensor device includes a plurality of electrode chambers, a measurement chamber, and an accommodation chamber which are proximately connected to each other in annular relationship permitting expansion and contraction, wherein the annular relationship has an ordering of elements of: the measurement chamber, next a first group of electrode chambers, next the accommodation chamber, next a second group of electrode chambers, and back to the measurement chamber,
   each of the plurality of electrode chambers having a measurement electrode,
   the measurement chamber having a biological potential measurement circuit which is connected with each measurement electrode via electrically conductive wiring for measuring biological potential of the user by using the measurement electrode, and
   the accommodation chamber having an internal protrusion, such that the wiring which connects at least one measurement electrode and the biological potential measurement circuit is provided around the protrusion, the wiring having a length which enables longitudinal feeding in accordance with an amount of elongation when the sensor device is elongated, wherein
   a maximum clearance S between the accommodation chamber and an adjacent one of the electrode chambers is greater than a maximum clearance R between any two adjacent electrode chambers among the plurality of electrode chambers.

2. A sensor device for measuring biological potential of a user, for use in a biological potential input interface system including: a determination circuit configured to determine a motion of the user from the biological potential of the user against a determination criterion which is prepared in advance, and generate a control signal corresponding to the motion; and a control circuit configured to control operation of an internal circuit of an appliance based on the control signal, wherein,
   the sensor device includes a plurality of electrode chambers, a measurement chamber, and an accommodation chamber which are proximately connected to each other in annular relationship permitting expansion and contraction, wherein the annular relationship has an ordering of elements of: the measurement chamber, next a first group of electrode chambers, next the accommodation chamber, next a second group of electrode chambers, and back to the measurement chamber,
   each of the plurality of electrode chambers having a measurement electrode,
   the measurement chamber having a biological potential measurement circuit which is connected with each measurement electrode via electrically conductive wiring for measuring biological potential of the user by using the measurement electrode, and
   the accommodation chamber having an internal protrusion, such that the wiring which connects at least one measurement electrode and the biological potential measurement circuit is provided around the protrusion, the wiring having a length which enables longitudinal feeding in accordance with an amount of elongation when the sensor device is elongated, wherein
   a maximum clearance S between the accommodation chamber and an adjacent one of the electrode chambers is greater than a maximum clearance R between any two adjacent electrode chambers among the plurality of electrode chambers.

3. The sensor device of claim 2,
   wherein the biological potential measurement circuit is able to detect the biological potential of the user which occurs in accordance with the motion of the user.

4. The sensor device of claim 3, wherein
   the determination circuit includes:
   a detection circuit configured to detect, when the biological potential measured by using the measurement electrodes satisfies a prestored detection criterion, that the user has made an intentional motion; and
   a motion determination circuit configured to, when the intentional motion is detected, determine the intentional motion of the user from the biological potential measured by using each measurement electrode against a determination criterion which is prepared in advance, and generate a control signal corresponding to the motion.

5. The sensor device of claim 3, wherein
   the determination circuit includes:
   a detection circuit configured to detect, when the biological potential measured by using the measurement electrodes satisfies a prestored detection criterion, a point in time at which the biological potential is measured; and
   a motion determination circuit configured to detect an intentional motion of the user against a determination criterion which is prepared in advance, from the biological potential in a time range after a predetermined time since the detected point in time.

6. The sensor device of claim 3, wherein each measurement electrode is provided in a respective one of the plurality of electrode chambers so as to be located on an inner peripheral surface of the sensor device being connected in annular relationship.

7. The sensor device of claim 3, wherein in the sensor device being connected in annular relationship, the measurement chamber and the accommodation chamber are placed in opposite positions from each other.

8. The sensor device of claim 3, wherein, in the sensor device being connected in annular relationship, the accommodation chamber is located in an asymmetric position from the measurement chamber with respect to a center of a circle.

9. The sensor device of claim 3, wherein the determination circuit refers to a prestored manipulation reference in generating a control signal corresponding to a motion of the user from the biological potential measured by using each measurement electrode.

10. A method to be performed in a biological potential input interface system, comprising the steps of:
  providing a sensor device with which to measure biological potential of a user; and
  determining a motion of the user from the biological potential of the user against a determination criterion which is prepared in advance, and generating a control signal corresponding to the motion; and
  controlling operation of an internal circuit of an appliance based on the control signal,
  the sensor device including a plurality of electrode chambers, a measurement chamber, and an accommodation chamber which are proximately connected to each other in annular relationship permitting expansion and contraction, wherein the annular relationship has an ordering of elements of: the measurement chamber, next a first group of electrode chambers, next the accommodation chamber, next a second group of electrode chambers, and back to the measurement chamber,
  each of the plurality of electrode chambers having a measurement electrode,
  the measurement chamber having a biological potential measurement circuit which is connected with each measurement electrode via electrically conductive wiring for measuring biological potential of the user by using the measurement electrode, and
  the accommodation chamber having an internal protrusion, such that the wiring which connects at least one measurement electrode and the biological potential measurement circuit is provided around the protrusion, the wiring having a length which enables longitudinal feeding in accordance with an amount of elongation when the sensor device is elongated, wherein
  a maximum clearance S between the accommodation chamber and an adjacent one of the electrode chambers is greater than a maximum clearance R between any two adjacent electrode chambers among the plurality of electrode chambers.

* * * * *